United States Patent [19]
Kirk

[11] Patent Number: 5,595,191
[45] Date of Patent: Jan. 21, 1997

[54] ADJUSTABLE PATIENT IMMOBILIZATION SYSTEM AND METHOD FOR PATIENT IMMOBILIZATION

[75] Inventor: John R. Kirk, Ramsey, N.J.

[73] Assignee: WFR/Aquaplast Corporation, Wyckoff, N.J.

[21] Appl. No.: 542,173

[22] Filed: Oct. 12, 1995

[51] Int. Cl.$^6$ ..................................... A61F 5/37
[52] U.S. Cl. ........................... 128/846; 128/870
[58] Field of Search ................... 128/845, 846, 128/857, 858, 870, 869; 606/130

[56] References Cited

U.S. PATENT DOCUMENTS

| | | | |
|---|---|---|---|
| 4,341,220 | 7/1982 | Perry | 606/130 |
| 4,846,173 | 7/1989 | Davidson | 606/130 |
| 4,979,519 | 12/1990 | Chavarria | 128/857 |
| 5,370,117 | 12/1994 | McLaurin | 128/857 |

Primary Examiner—Michael A. Brown
Attorney, Agent, or Firm—W. Patrick Quast, Esq.

[57] ABSTRACT

A patient immobilization system and method for patient immobilization prior to radiation therapy is described. An adjustable anchor including a slidable base plate between left and right sides of the anchor, provides for utilizing the same patient immobilizing device for head and neck, chest, and pelvis areas requiring radiation treatment. The adjustable anchor accommodates varying sizes of customized posterior molds forming the "mattress" portion of the patient immobilization system, while customized anterior molds secured in a holder are fitted over the patient area to be directly exposed to radiation. The holder is then firmly, but easily releasably secured to the adjustable holder. A hook and loop fastener or compression clip assembly provides for quick release of the anterior mold from the patient when required for difficult or emergency situations.

20 Claims, 9 Drawing Sheets

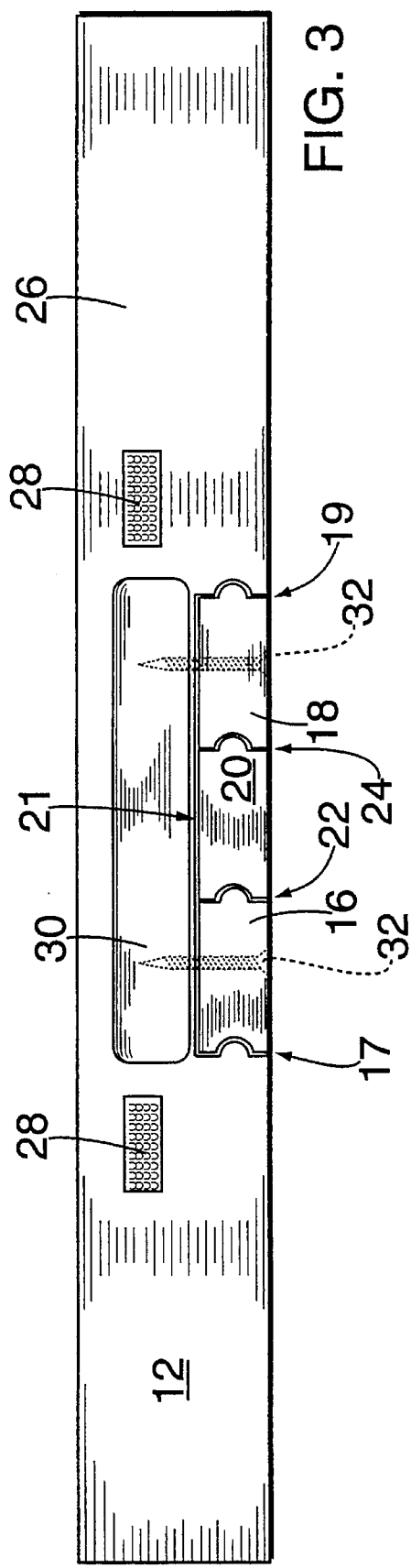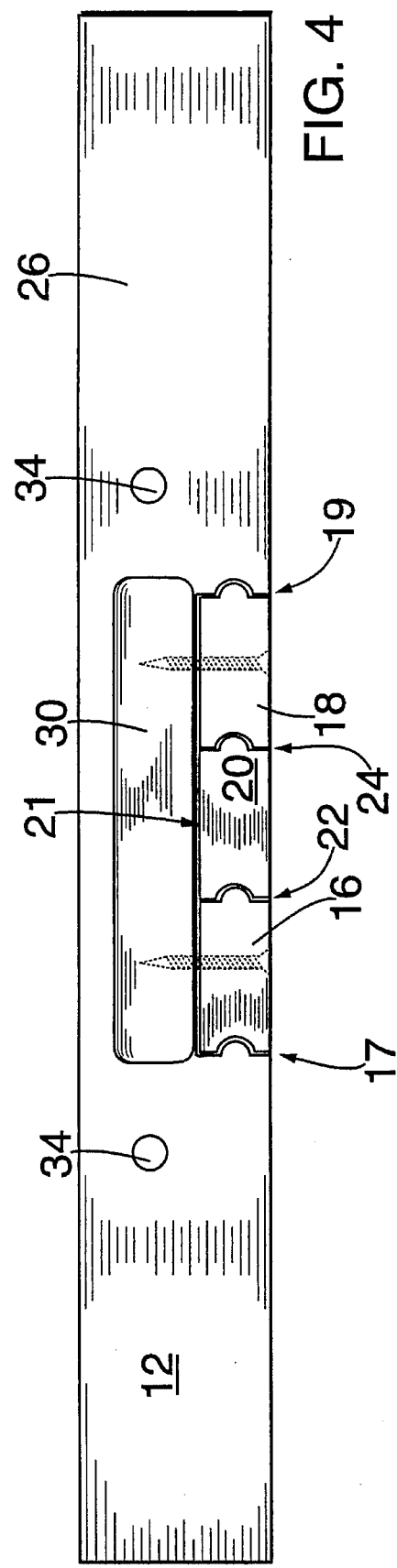

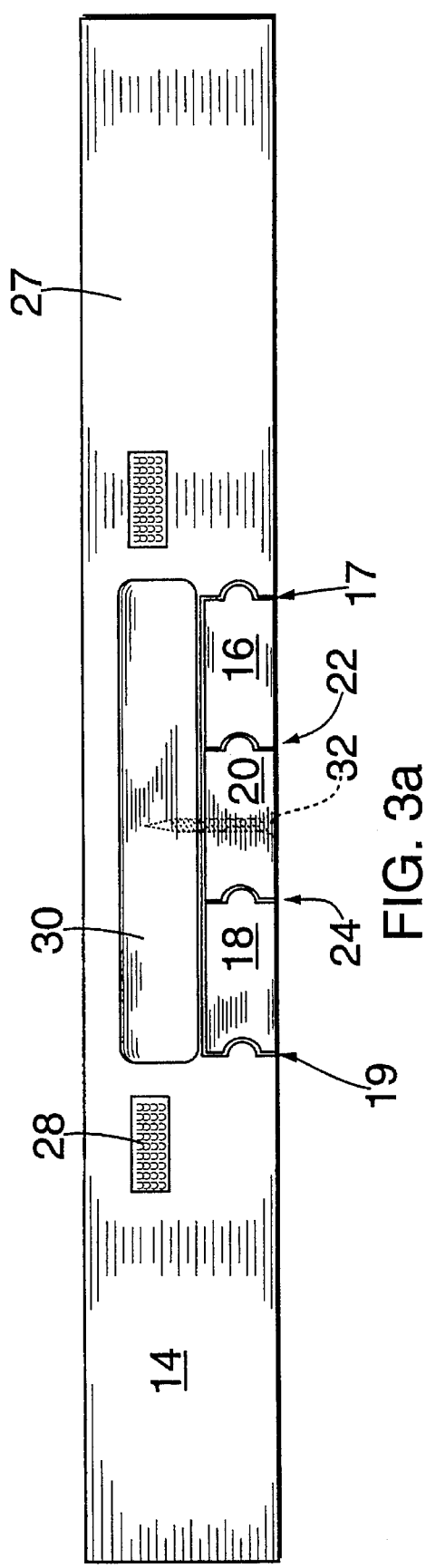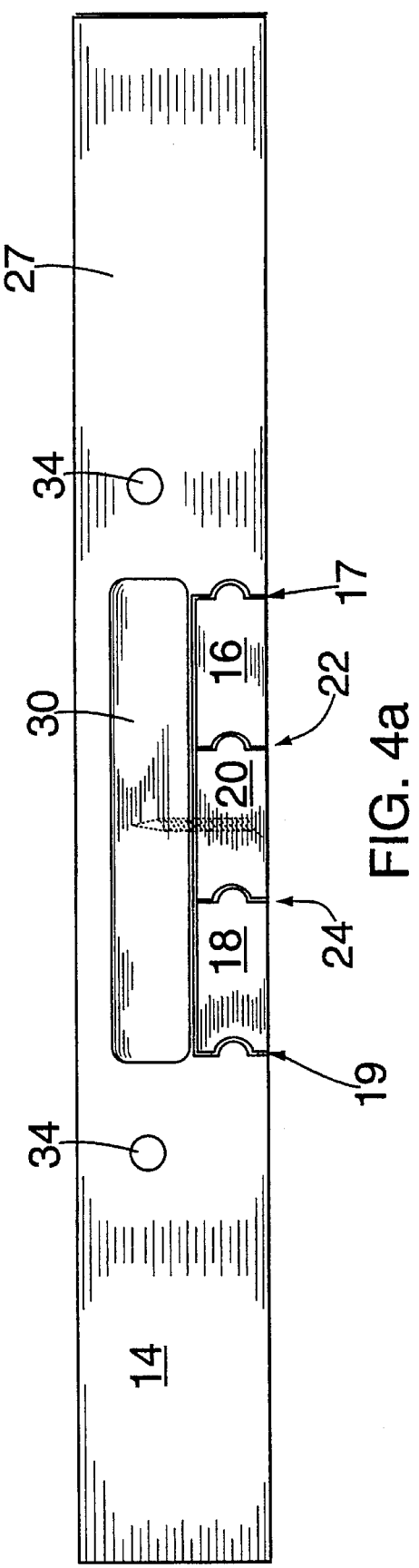

ADJUSTABLE PATIENT IMMOBILIZATION SYSTEM AND METHOD FOR PATIENT IMMOBILIZATION

BACKGROUND

This invention relates to systems for immobilizing a patient immediately prior to receiving radiation therapy, and in particular to a system and method that is adjustable for the head and neck, chest, or pelvis areas of the patient.

Radiotherapy has today become increasingly more precise, this greater precision necessitating reliable patient immobilizing systems. Typically patients undergoing radiation therapy for tumors and other conditions receive small doses of radiation repeatedly, often over extended periods of time. It is important to the success of the treatment for the patient to be comfortably repositioned accurately for these numerous treatment periods.

Past attempts by clinicians to position patients involved laser beams aimed at skin marks drawn on the patient, then immobilizing the patient with adhesive tape, plaster of paris, or strips of VELCRO (a registered trademark of VELCRO USA). These techniques were time consuming for the clinician and caused unsightly skin marks and adhesive tape irritation for the patient. In addition, these methods were difficult to perform on very young, old, or confused patients.

In recent years more precise and comfortable positioning and immobilization devices have been employed, fabricated from wood or plastic materials, plaster or fiberglass bandage materials, vacuum formed high temperature plastics, hand formable low temperature plastics, bite blocks, foamed in place urethane shells, and vacuum bags filled with polystyrene pellets which shape to the patient. For example, in current practice a hand formable thermoplastic material such as AQUAPLAST (a registered trademark of WFR Aquaplast Corporation) creates a customized anterior mold (a mold interposed on the skin of the patient between the patient and the source of radiation) of a portion of the patient, such as the face, chest, or pelvis area. This anterior mold is often used with a posterior mold (a mold in the shape of the patients head and neck, chest area, and so on, with the body of the patient positioned between this posterior mold and the source of radiation) acting as a mattress for comfortably supporting the patient during treatment. This posterior mold can be fabricated using a urethane foam to cast a body impression, or by use of a flexible vacuum bag containing pellets, such as polystyrene, which, when subjected to a vacuum, cause the shape of the patient to be formed in the vacuum bag.

While these current devices and techniques provide greater patient comfort and accuracy in patient repositioning prior to radiation therapy, they do not address the unique system and method of the instant invention for anchoring differently sized anterior and posterior molds together for fast, comfortable, and economical patient repositioning during radiation therapy.

It is therefore a primary object of the invention to provide an adjustable anchor for securing anterior and posterior molds to a patient for accurate repositioning of said patient during radiation therapy.

An additional object of the invention is to provide a single device for anchoring anterior and posterior molds for head and neck, chest, or pelvic patient immobilization set ups.

A further object of the invention is to provide a compatible device for anchoring virtually all currently available patient immobilization devices.

Another object of the invention is to provide a compatible anchoring device to provide a simple, inexpensive upgrade to achieve greater precision for existing immobilization equipment.

Still another object of the invention is to simplify immobilization equipment requirements for new or expanding treatment facilities so as to reduce capital expenditure for more specialized equipment.

A further object of the invention is to provide an adjustable anchor for customized anterior and posterior molds, said anchor providing for quick patient release to prevent patient injury during difficult or emergency treatment situations.

SUMMARY

These and other objects are obtained with the instant invention of the patient immobilization system and method for patient immobilization.

A current technique for immobilizing a patient in a manner such that this exact position can be recreated timely and conveniently involves, as for example in immobilizing a patient's head and neck area, making a perforated face mask of the patient's face. This is performed by first softening an easily thermoformable perforated plastic sheet, such as AQUAPLAST (available from WFR Aquaplast Corporation, P.O. Box 635, Wycoff, N.J. 07481), in warm water, placing the softened plastic sheet over the face of the patient, and then gently manually forming the sheet by a clinician so as to have the sheet conform to the surface facial characteristics of the patient. The plastic sheet then hardens, and can be repeatedly reused again in future treatment sessions with this patient. At approximately the same time as the facial mold or anterior mold is being formed for the patient, a posterior mold or supporting mattress, in this case for the head and neck of the patient, is constructed. This supporting mattress can be fabricated by various techniques, including a customized urethane foam mold of the patient's head and neck, or a customized impression of the patient's head and neck formed by creating a vacuum in a vacuum bag filled with plastic pellets, such as polystyrene pellets. In this manner both the anterior mold and the posterior mold can be used repeatedly on the same patient in an attempt to irradiate precisely this same area in each treatment session of the patient. Obviously, these same techniques are employed for anterior and posterior molds of other parts of the body, including the chest and pelvis area.

To the present time devices for securing anterior and posterior molds together have been highly specific, such as, for example, only for the head and neck area. Also, specific clamping mechanisms have been devised to secure the anterior and posterior molds together, with little thought given to multi-purpose devices or for quick release of the patient when required.

It has been found that virtually all of the currently commercially available patient immobilization equipment can be accommodated by the adjustable anchoring device of the invention. A prototype of the device has been constructed in wood to demonstrate its utility. Two, foot long lengths of wood form the left and right side of a frame. The two sides are parallel to each other with an adjustable base plate in between. The base plate is comprised of three flat sections of wood, two sections being permanently affixed to one side, with a third section which comprises the middle portion of the base plate being permanently affixed to the other side. The three base plate sections are configured at their longitudinal edges so as to form a tongue and groove joint with each other, and with matching openings in the upstanding wall portion of the left side and right side members. In this manner the left side and right side can be manually caused to be contracted so as to actually be touching one another, or expanded apart a considerable spaced distance. Posterior molds for virtually all portions of the body, including head and neck, chest, or pelvis are all easily and quickly accommodated within this one anchoring device.

Modified holders for securing the left and right sides of the anterior mold, as, for example, the head and neck mold described above, are provided to cooperate with the adjustable anchor of the invention so as to provide a quick release mechanism for the patient. Each of two required holders is preferably fabricated in a sterilizable plastic, such as high density polyethylene, polycarbonate, or nylon. Each holder is comprised of two lengths of plastic so that an edge of an anterior mold can be secured between the two lengths. As will be more fully described each length of each holder has two threaded holes for securing the two lengths together, with the anterior mold sandwiched in between. With both the left and right edges of the anterior mold secured in the two holders, the holders form a frame for the now rigid sheet of plastic forming the anterior mold.

The two anterior mold holders together with the anterior mold, can now be affixed to the adjustable anchor of the invention, the base plate of which now secures the posterior mold with the lateral edges of the posterior mold securely in contact with the two sides of the anchor. Since a quick release mechanism between the holders and the anchor was deemed important to the invention, two methods were tested. In a first method a hook section of a hook and loop fastening fabric, such as VELCRO, was adhesively secured to a side of each holder that is to be secured to the anchor, with a matching loop section of a hook and loop fastening fabric being adhesively secured to the outer edges of each of the two upstanding side walls of the sides of the anchor. The side walls of the anchor are configured to have a convenient hand grip cut out so that when the anterior mold is secured to the anchor a clinician can at any time grasp either the left or right side of the anterior mold holder and cause it to quickly release from the anchor without any danger of harm to the patient. Similarly, a patient can be instructed as to how to use this quick release mechanism, adding a reassuring note for the patient during the radiation procedure.

In a second method employed for quick release of the holders from the anchor two nylon compression clips are secured to each holder. Compression clips are similar in shape to a standard bolt, except that the extended shaft of the bolt has a hollowed out portion along the length of the shaft. These compression clips are fabricated in a plastic, such as nylon, having good memory characteristics. When the shaft of the clip is pushed through a pre-cut hole it immediately expands to its original shape when it is free of the hole. Two such clips, affixed to one side of each holder which is to face the upstanding side wall of the anchor, then provides for a simple and effective quick release connection when connected to matching holes in the left and right upstanding side walls of the anchor. As in the case of the hook and loop fabric fastener, these compression clips provide the clinician or the patient with a safe, easy method for removing the anterior mold from the patient for troublesome or emergency situations.

The procedure for utilizing the complete patient immobilization system of the invention is as follows:

1. A posterior mold of the patient is made for the area of therapeutic interest.

2. The posterior mold is placed on the base plate of the anchor, and the sides of the anchor are adjusted to secure the lateral edges of the posterior mold.

3. An anterior mold of the patient is made for the area of therapeutic interest.

4. With the patient comfortably positioned on the posterior mold, the anterior mold is placed on the patient and affixed to the sides of the anchor by means of the holders for the anterior mold in a secure but easily releasable manner. The treatment period can now begin.

5. After the treatment period, the posterior and anterior molds are set aside, at the ready for fast and simple set up using the adjustable anchor of the invention so as to assure precise re-radiation of the same area as previously treated.

Thus a new and economical convenience is provided for a wide variety of currently commercially available patient immobilization systems. Customized posterior and anterior molds for different sized body areas, including the head and neck, chest, and pelvis area can now be efficiently and accurately repositioned utilizing the adjustable anchor. At the same time the built-in quick release mechanism for the anterior mold provides added reassurance to both the clinician and the patient.

The methods for making anterior and posterior patient immobilizing molds described above are conventional, and well known to the art. The adjustable anchor of the invention has been described as fabricated in wood, and obviously other materials, such as carbon fibre or plastics, can be similarly employed.

BRIEF DESCRIPTION OF THE DRAWINGS

FIG. 3 is an elevated view of the left side of the adjustable anchor depicted in FIG. 1, illustrating a first version of a fastener securing an anterior mold to the adjustable anchor.

FIG. 3A is an elevated view of the right side of the adjustable anchor depicted in FIG. 1, illustrating a first version of a fastener securing an anterior mold to the adjustable anchor.

FIG. 4 is an elevated view of the left side of the adjustable anchor depicted in FIG. 1, illustrating a second version of a fastener for securing an anterior mold to the adjustable anchor.

FIG. 4A is an elevated view of the right side of the adjustable anchor depicted in FIG. 1, illustrating a second version of a fastener for securing an anterior mold to the adjustable anchor.

DETAILED DESCRIPTION

Figure 1:
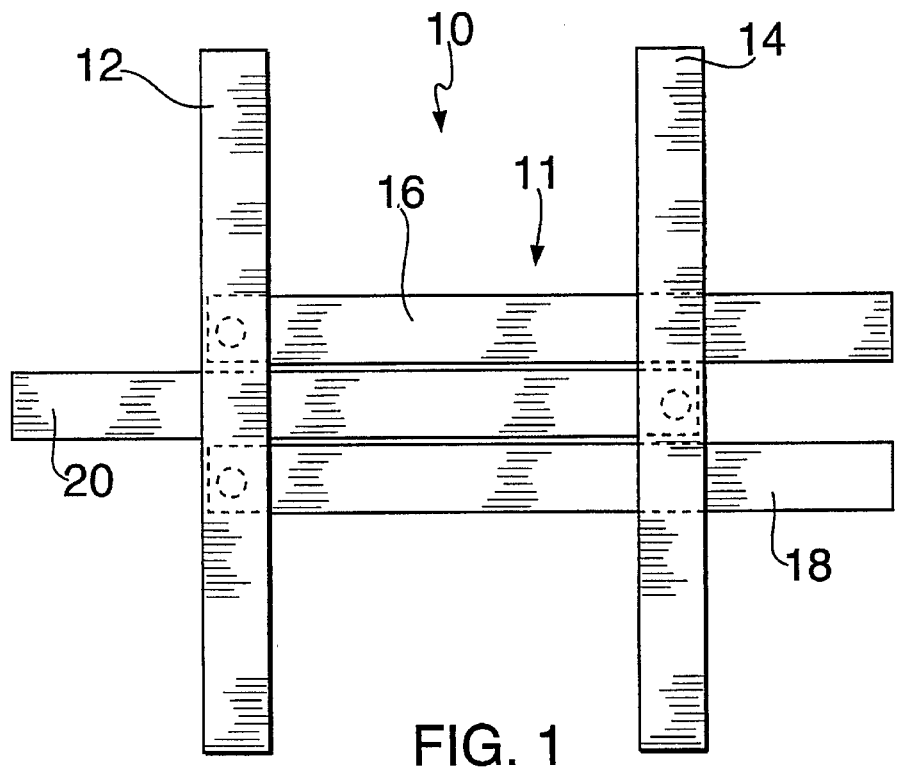
FIG. 1 is a top plan view of one version of the adjustable anchor of the invention, illustrating the adjustable feature of the base plate for encompassing a smaller area.
Figure 2:
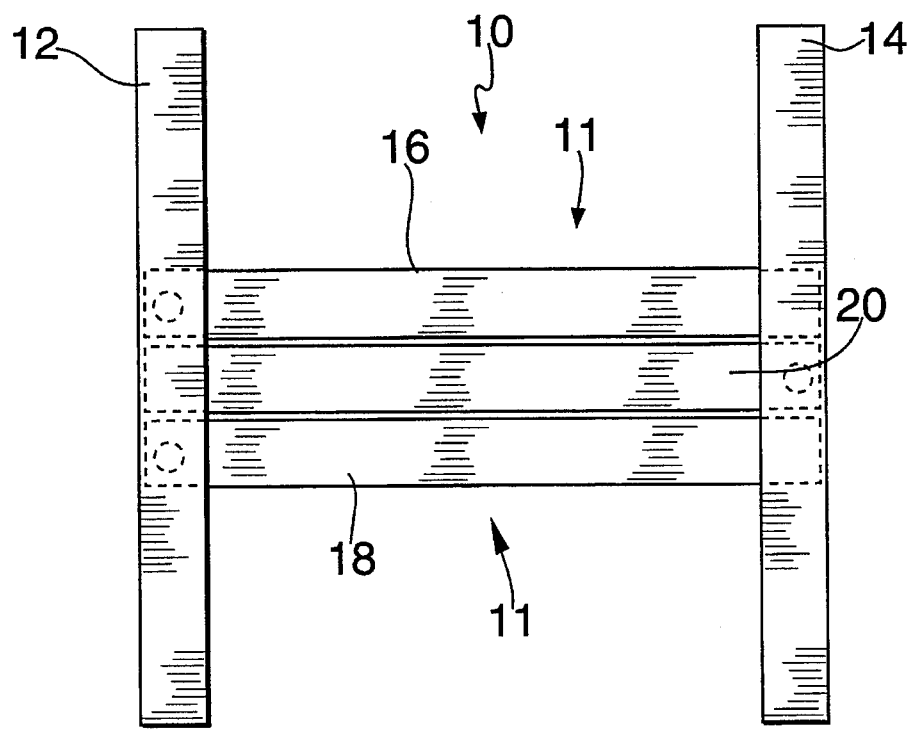
FIG. 2 is a top plan view similar to FIG. 1, illustrating the base plate as further extended.

Referring now to the drawings wherein similar structures having identical functions are denoted with the same numeral, FIGS. 1–4 illustrate a typical version of the adjustable anchor 10 of the invention. The device shown is fabricated in wood, having a left and a right side (12,14) and a base plate 11. Typical dimensions for both the left and right sides would be 12" L×1× W×2" H. The base plate 11 is shown as comprised of three sections of wood (16,18,20), each of the three sections being approximately 11" L×2" W×½" H. A top base plate section 16 and a bottom base plate section 18 are permanently affixed to one side 12 of the anchor by any convenient means such as a screw 32 (FIG. 3) between the top or bottom base plate section and the side to which it is affixed. The middle section 20 of the base plate is positioned between the top and bottom base plate sections, being similarly permanently affixed to the other side 14 of the anchor (FIG. 3A). Tongue and groove joints 17 and 19 at respective outside lateral edges of the sections, 16 and 18 of the base plate and the sides 12 and 14; and tongue and groove joints, 22 and 14 between lateral edges of section 20 of the base plate and sections 16 and 18, respectively, of the base plate permit perpendicular motion of the sections relative to the sides of the anchor as best seen in FIGS. 3, 3A, 4, and 4A. As shown in FIG. 1 the area encompassed by the base plate can be decreased by sliding the middle section 20 through the opening 21 (see FIG. 3) and the tongue and groove joints 22 and 24, while at the same time the top section 16 and bottom section 18 slide out of the right side 14 of the anchor guided by tongue and groove joints 17 and 19 as well as joints 22 and 24. Similarly the tongue and groove joints and openings in the anchor provide for moving the left and right sides of the anchor apart while maintaining their parallel relationship until a maximum area is encompassed by the base plate. Obviously a variety of other materials other than wood can be employed to fabricate the adjustable anchor of the invention, as, for example, carbon fibre or a plastic material. The mechanism described for expanding or contracting the area of the base plate is, of course, only indicative of one possible means for making this area adjustable. For example, the base plate can be fabricated to move in unison left or right relative to the sides of the anchor, or to compress or expand in accordion like manner, and so on.

Figure 5:
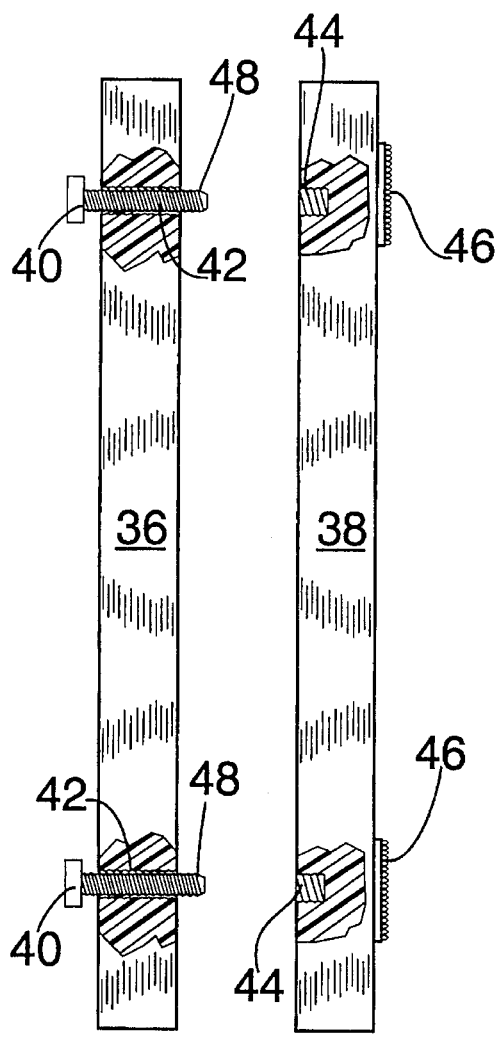
FIG. 5 is a top plan view of one version of anterior mold holders, illustrating a first version of a fastener for securing the holder to the adjustable anchor.
Figure 6A:
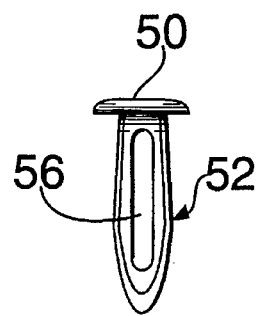
FIG. 6A illustrates a compression clip employed in FIG. 6 for securing the holders to the adjustable anchor.
Figure 6:
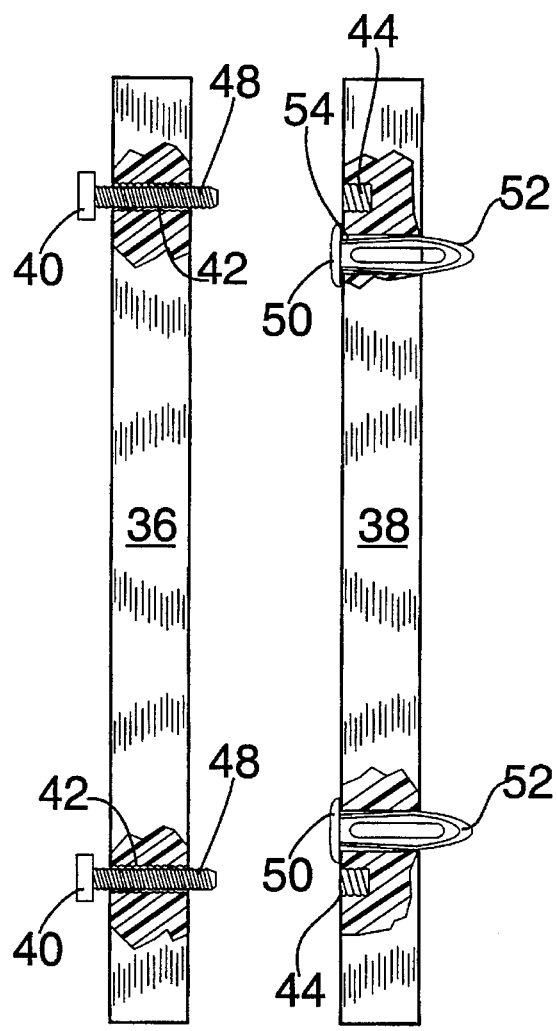
FIG. 6 is a top plan view of one version of anterior mold holders, illustrating a second version of a fastener for securing the holders to the adjustable anchor.

FIGS. 5, 6, and 6A illustrate two versions of a quick release anterior mold holder suitable for use in conjunction with the adjustable anchor of the invention. The holder consists of two similarly sized lengths 36, 38 of material, preferably fabricated in a sterilizable plastic. The purpose of the holder is to provide means for securing either a left or right side of an anterior mold prior to placing the anterior mold over the patient and securing this mold to the adjustable anchor. One structure that can be employed to this end is to have two screws 40 connected at either end of a first section 36, with matching screw holes 44 in a second section 38. Placing the left and right sides of an anterior mold 58 (FIG. 8) into two such holders, and then tightening the screw shafts 48 through the threaded openings 42, 44 in both the first 36 and second 38 holder sections now secures the sides of the anterior mold 58 within the two holders (FIG. 8). As best seen in FIGS. 3, 3A, and 5 a first mechanism for securing the holders to the anchor can be a hook and loop fabric fastener such as VELCRO. As illustrated in FIG. 5 sections of a hook portion 46 of the fabric can be affixed to the second holder section 38, and then be conveniently connected to a loop portion 28 of the fabric affixed to either the left 26 (FIG. 3) or right 27 (FIG. 3A) upstanding wall of the sides of the anchor. This structure will now provide for quick release of the anterior mold 58 from the patient by means of the hand cut out 30 (FIG. 7) on both sides of the anchor by either the clinician or the patient.

A second mechanism for securing the holders to the anchor can be a compression clip 50 as illustrated in FIGS. 6 and 6A. Compression clips utilized in the invention are a type of bolt having a hollowed out portion 56 in the shaft 52 of the bolt so that the shaft 52 is compressed when it passes through pre-punched hole 54, then springs back to its original shape when free of the hole 54. Clips of this type can be fabricated in metal, or plastics such as, for example, nylon. Compression clips suitable for this invention are available from Micro Plastics, Inc., Flippin, Ark. 72674. In FIG. 6 two clips are shown a spaced distance apart connected to the second section 38 of a holder. The clips, when inserted into matching openings 54 in the upstanding left 26 and right 27 side walls of the anchor now provide for firmly securing the holder to the anchor, yet at the same time permit quick release of the holder from the anchor by making use of the hand grip cut out 30 at both sides of the anchor.

Figure 7:
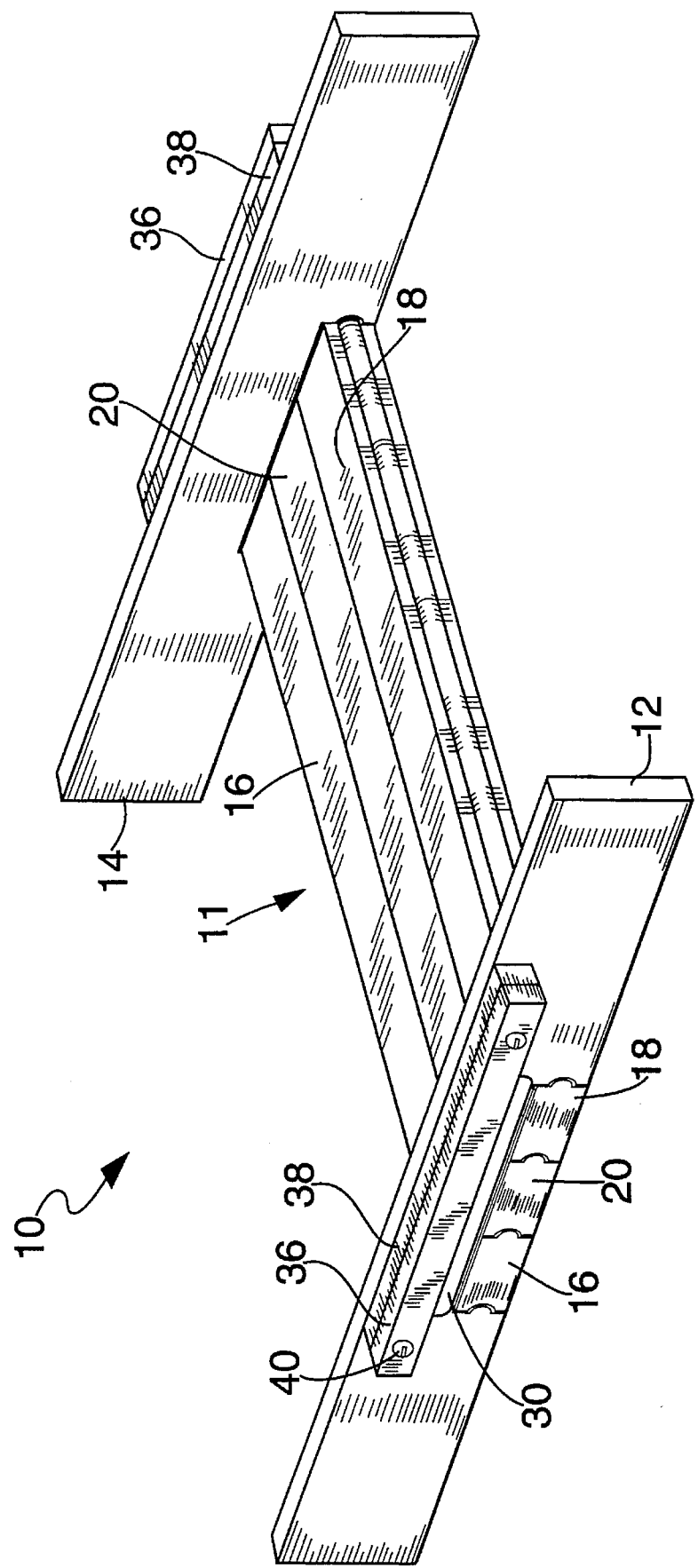
FIG. 7 is an oblique elevational perspective view of one version of the adjustable anchor of the invention, illustrating anterior mold holders secured to the sides of the anchor.
Figure 8:
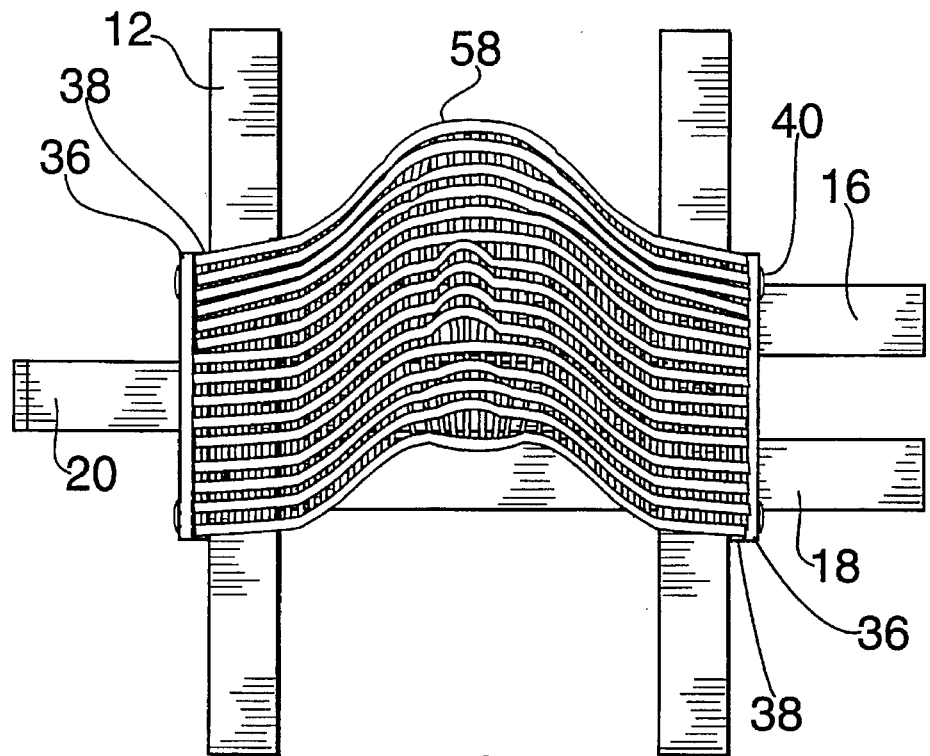
FIG. 8 is a top plan view of one version of the anterior mold holders shown securing a mold for the surface of a human face.
Figure 9:
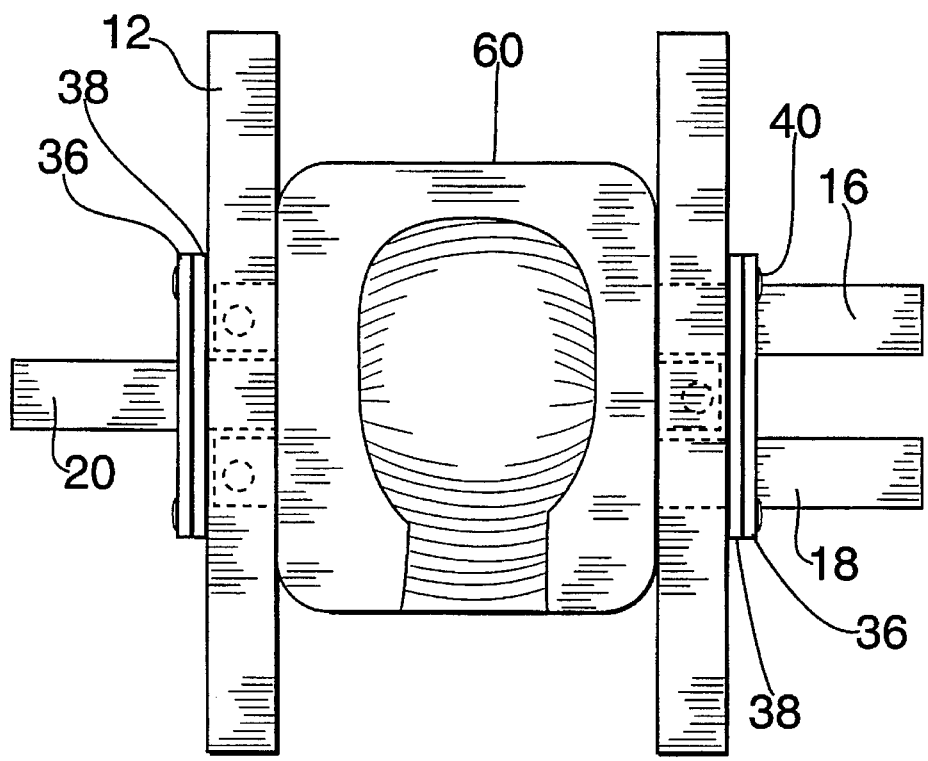
FIG. 9 is a top plan view of one version of the adjustable anchor of the invention, shown adjusted to accommodate a head and neck area posterior mold.

FIG. 7 illustrates both the first 36 and second sections 38 of two holders (without the anterior mold secured therebetween) as secured to the sides of the anchor, with screws 40 holding each of the two sections of each holder together, with the holders themselves being secured to the anchor by either of the two mechanisms described above (hook and loop fabric or compression clip-not shown). In FIG. 8 a formed anterior facial mold 58 is shown with its left and right sides securely held between the two sections of each of the two holders. In FIG. 9 a posterior mold 60 of the rear portion 62 of a patient's head and neck is shown as being placed on the base plate 11, and correctly positioned between the left side 12 and the right side 14 of the anchor by manually adjusting the sections of the back plate to the proper width.

Figure 10:
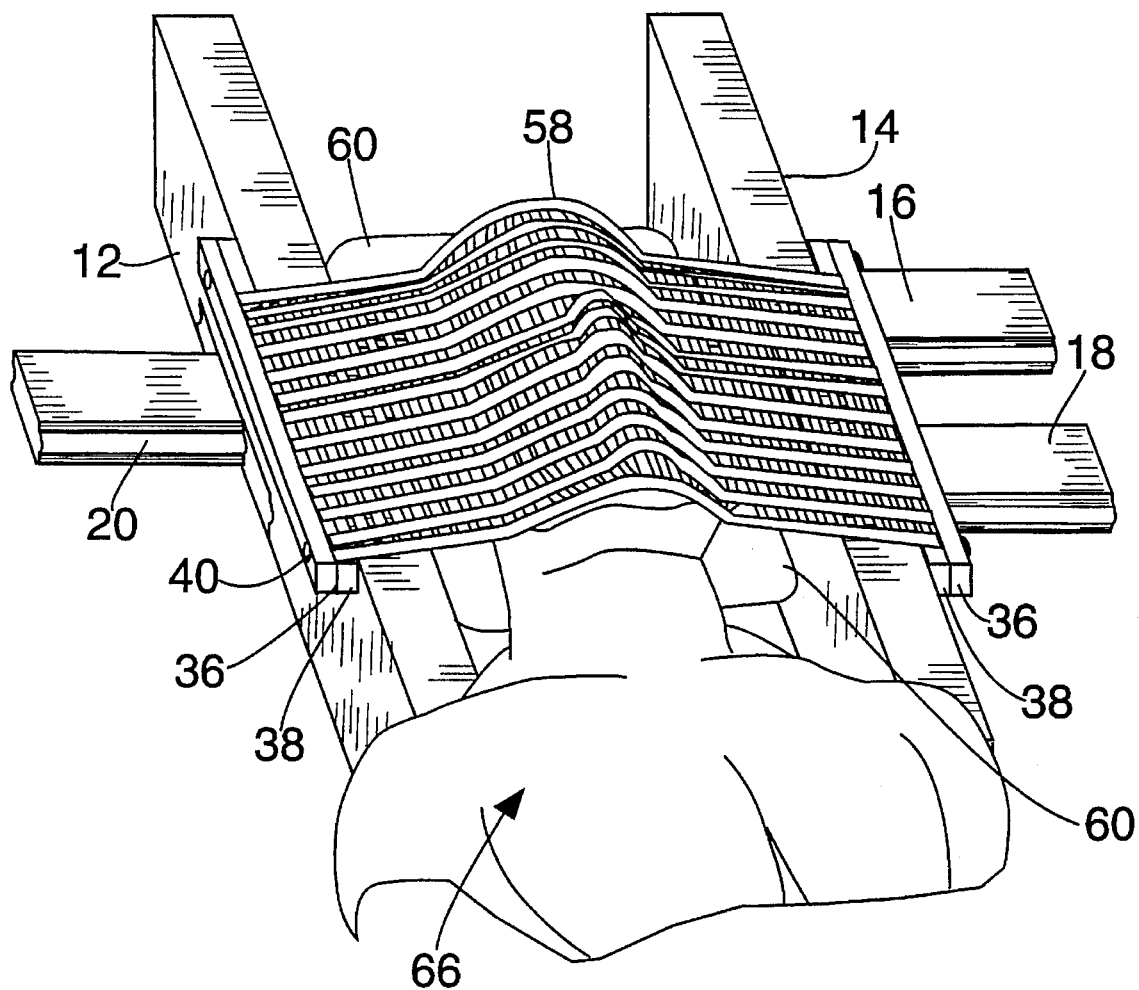
FIG. 10 is a top plan, perspective view of one version of the patient immobilization system of the invention shown adjusted to and securely positioning a customized posterior head and neck mold with an anterior face mold secured in the holders in place on a patient.
Figure 11:
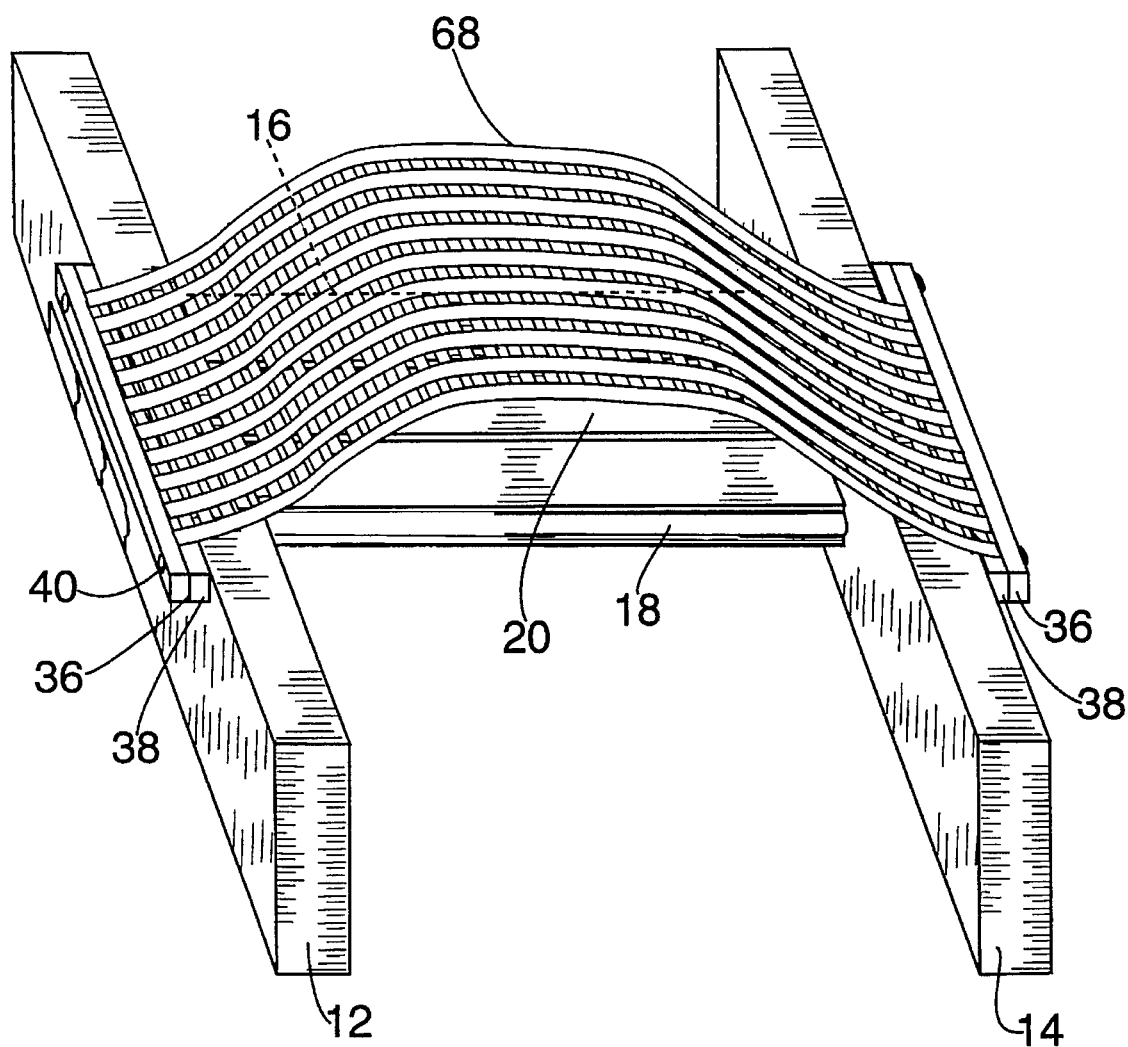
FIG. 11 is a top plan, perspective view of one version of the patient immobilization system of the invention, illustrating the anchor as expanded to accommodate a larger anterior mold secured by the anterior mold holders.
Figure 11A:
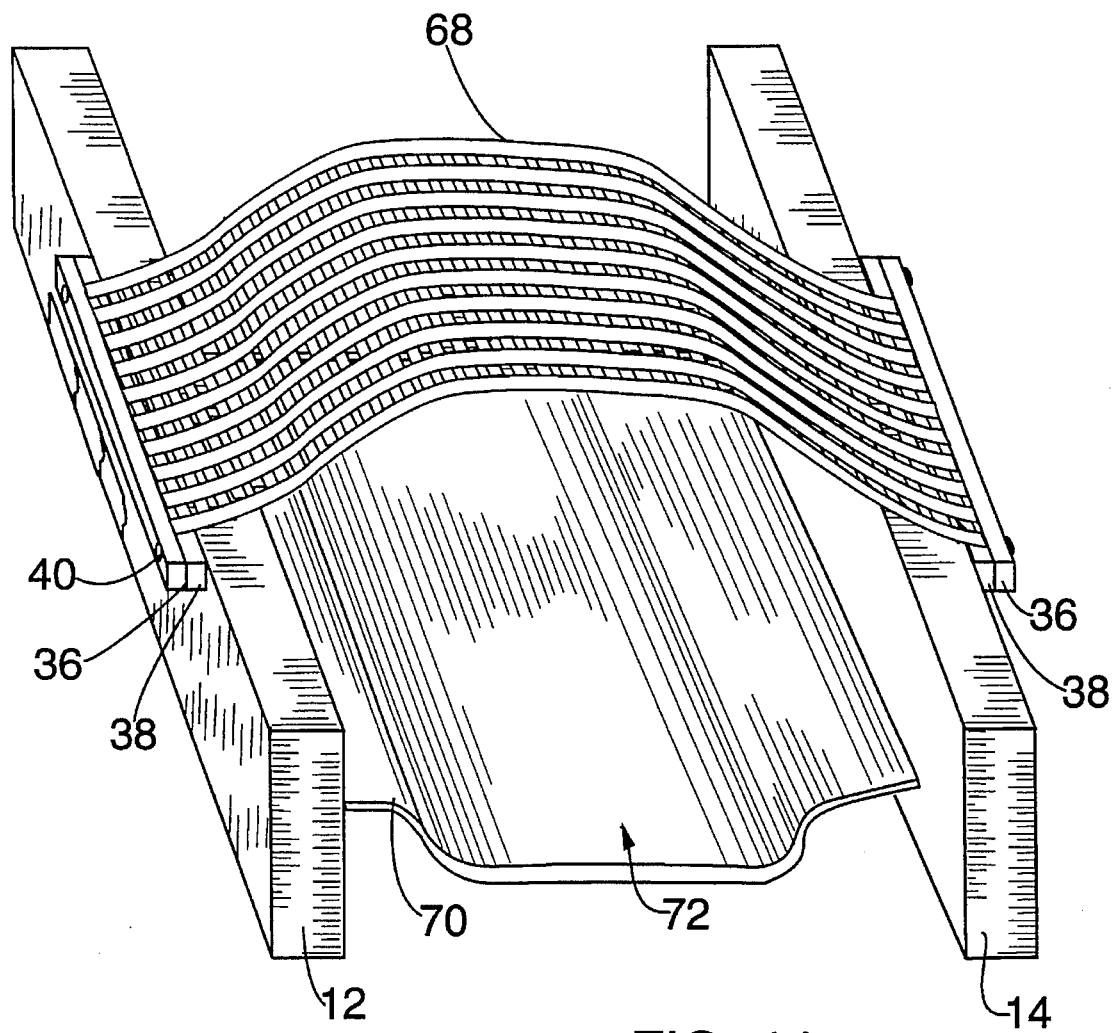
FIG. 11A illustrates the patient immobilization system depicted in FIG. 11 with a customized urethane foam posterior mold in place on the base plate of the anchor, and adjustably secured in place by the anchor of the invention with the customized anterior mold.

FIGS. 10–11A illustrate the complete patient immobilizing system of the invention. In FIG. 10 a patient 66 is shown as comfortably and accurately repositioned prior to receiving radiation therapy. The rear portion of the patient's head and neck is supported on a customized posterior mold 60, with a customized anterior mold 58 in place matching the contours of the patient's face. Both molds are shown secured and accurately positioned by the cooperation of the adjustable anchor and two anterior mold holders. In FIG. 11 the adjustable anchor is shown further extended in order to accommodate a large, customized chest area anterior mold 68, with FIG. 11A illustrating the complete patient immobilizing system of the invention showing a customized posterior mold 70 with the back area 72 of the patient pre-formed in the mold. These larger scale posterior and anterior molds are secured utilizing the same adjustable anchor and anterior mold holders as in the case of the illustrated head and neck posterior and anterior mold.

Thus it can be seen that the instant invention provides a new convenient, economical, and accurate patient immobilizing system for radiation therapy. Virtually all existing patient immobilizers can be accommodated with the adjustable anchor of the invention. In addition, the invention provides an important new safety feature for the clinician and patient with the incorporated anterior mold quick release mechanisms described.

While the present invention has been disclosed in connection with preferred versions shown and described in detail, various modifications and improvements thereon will become readily apparent to those skilled in the art. Accordingly, the spirit and scope of the present invention is to be limited only by the following claims.

What is claimed is:

1. An adjustable anchor for securing differently sized combinations of anterior and posterior molds of a customized patient immobilizing system to patients prior to said patients receiving radiation therapy, comprising:

(a) said anchor having a left side and a right side, with a base plate connected therebetween;

(b) said left and right sides being substantially parallel to each other;

(c) said base plate defining a substantially flat area between said left side and said right side, said base plate having means for cooperating with said left side and said right side in order to enable said base plate to be expanded or contracted in a direction perpendicular to said sides so that different widths of said anterior-posterior mold combinations are accommodated; and (d) means for securing said anterior mold to at least one side of said anchor.

2. The adjustable anchor according to claim 1 wherein said base plate has a left side adjacent said left side of said anchor, and a right said adjacent said right said of said anchor, and at least a first and a second section, said base plate including aligning means on the edges of said first and second sections of said base plate, said aligning means cooperating with a complementing aligning means within an opening for an end of said first and second sections of said base plate within a side of said anchor, so that said left and said right sides of said anchor can be moved towards or away from each other in a parallel relationship, thereby decreasing or increasing the area between said left side and said right side of said anchor encompassed by said base plate.

3. The adjustable anchor according to claim 1 wherein said base plate comprises at least three sections, a first and third section of said at least three sections being fixedly secured at one end to the same respective side, left or right, of said anchor, a second section of said at least three sections being fixedly secured at one end to the opposite side of said respective side to which said first and third sections are fixedly secured, the other end of said first, second, and third sections being free, said base plate including aligning means, said adjustable anchor when assembled including said second section disposed between said first and third sections, said adjustable anchor further including complementing aligning means disposed between said first and second sections, between said second and third sections, and between at least, said first section and an opening in the side of said anchor to which said second section is fixedly secured, so that said left and said right sides of said anchor can be moved towards or away from each other in a parallel relationship, thereby decreasing or increasing the area between said left side and said right side of said anchor encompassed by said base plate.

4. The adjustable anchor according to claims 1, 2, or 3 wherein said means for securing said anterior mold to at least one side of said anchor includes means for quick release of said means for securing to said anchor when said anterior mold is secured to said anchor.

5. The adjustable anchor according to claim 4 wherein said differently sized combinations of anterior and posterior molds comprise customized molds for head and neck, chest, or pelvis areas of a patient.

6. The adjustable anchor according to claim 5 wherein said customized anterior mold is formed from a sheet of hand formable thermoplastic material.

7. The adjustable anchor according to claim 4 wherein said means for quick release comprises a complementing hook and loop fastener secured to cooperating sides of said anchor and said means for securing said anterior mold.

8. The adjustable anchor according to claim 4 wherein said means for quick release comprises one or more compression clips secured to at least one side of said means for securing, with matching holes for the shaft of said clips built into the cooperating side, for said one side of said means for securing of said anchor.

9. An adjustable anchor for securing differently sized combinations of anterior and posterior molds of a customized patient immobilizing system to patients prior to said patients receiving radiation therapy, comprising:

(a) said anchor having a left side and a right side, with a base plate connected therebetween;

(b) said left side and right sides being substantially parallel to each other;

(c) said base plate defining a substantially flat area between said left side and said right side, said base plate having means for cooperating with said left side and said right side in order to enable said base plate to be expanded or contracted in a direction perpendicular to said sides so that different widths of said anterior-posterior mold combinations are accommodated; and (d) said left side and said right side of said anchor having means for securing holders for said anterior mold, wherein said base plate comprises at least two sections, each of said sections being substantially greater in length than in width, each of said sections being secured at one end to a respective side of said anchor and free at its other end, each of said sections having a tongue and groove joint along at least one lateral edge cooperating with a matching tongue and groove joint within an opening for said free end of said section built into a side of said anchor.

10. The adjustable anchor according to claim 9 wherein said anchor and said holder further comprise means for quick release of said holders from said anchor when said holders are secured by said anchor.

11. The adjustable anchor according to claim 10 wherein said means for quick release of said holders from said anchor when said holders are secured by said anchor comprises a hook and loop fabric fastener secured to the inner surface of both the left side and right side of each of said holders and the outer surface of said left side and said right side of said anchor.

12. The adjustable anchor according to claim 10 wherein said means for quick release of said holders from said anchor when said holders are secured by said anchor comprises one or more compression clips secured to the left side and the right side of each of said holders, with matching holes for the shaft of said clips built into the outer surface of said left side and said right side of said anchor.

13. A method for accurately repositioning patients for radiation therapy in differently sized customized anterior and posterior molds utilizing the same adjustable anchor for said differently sized molds, comprising the steps of:
   (a) placing said posterior mold on a base plate of said adjustable anchor, said anchor having a left side and a right side, between said left side and said right side of said anchor;
   (b) adjusting said base plate and said left side and said right side of said anchor so that any one of said left side and said right side combinations of said differently sized posterior molds is secured by said anchor;
   (c) placing said customized anterior mold over an area of said patient conforming to said customized anterior mold; and
   (d) securing said customized anterior mold to said anchor.

14. The method according to claim 13 further comprising the step of quickly releasing said patient from said customized anterior mold when emergency circumstances require such release.

15. The method according to claim 14 wherein said step of quickly releasing said patient from said anterior mold comprises utilizing a hook and loop fabric fastener on said anterior mold and said adjustable anchor.

16. The method according to claim 14 wherein said step of quickly releasing said patient from said anterior mold comprises utilizing compression clips on said anterior mold and matching holes for the shaft of said clips in said adjustable anchor.

17. A method for accurately repositioning patients for radiation therapy in differently sized anterior and posterior molds utilizing the same adjustable anchor and anterior mold holders for said differently sized molds, comprising the steps of:
   (a) placing said posterior mold on a base plate of said adjustable anchor, said anchor having a left side and a right side, between said left side and said right side of said anchor;
   (b) adjusting said base plate and said left side and said right side of said anchor so that any one of said left side and said right side combinations of said differently sized posterior molds is secured by said anchor;
   (c) securing said left side and said right side of any one of said left side and said right side combinations of said differently sized anterior molds in anterior mold holders;
   (d) placing said customized anterior mold over an area of said patient conforming to said customized anterior mold; and
   (e) securing said customized anterior mold in said anterior mold holders to said adjusted anchor.

18. The method according to claim 17 further comprising the step of quickly releasing said patient from said customized anterior mold when emergency circumstances require such release.

19. The method according to claim 18 wherein said step of quickly releasing said patient from said anterior mold comprises utilizing a hook and loop fabric fastener on said anterior mold holders and said adjustable anchor.

20. The method according to claim 18 wherein said step of quickly releasing said patient from said anterior mold comprises utilizing compression clips on said anterior mold holders and matching holes for the shaft of said clips in said adjustable anchor.

* * * * *

UNITED STATES PATENT AND TRADEMARK OFFICE
CERTIFICATE OF CORRECTION

PATENT NO. : 5,595,191
DATED     : January 21, 1997
INVENTOR(S) : John R. Kirk, Ramsey, New Jersey It is certified that error appears in the above-identified patent and that said Letters Patent is hereby corrected as shown below:

IN THE CLAIMS: At column 7, line 46, change the word "said", first and third occurrence to --side--.

Signed and Sealed this

Eighth Day of April, 1997

Attest:

BRUCE LEHMAN

*Attesting Officer*     *Commissioner of Patents and Trademarks*